United States Patent [19]

Alpegiani et al.

[11] Patent Number: 4,508,649
[45] Date of Patent: Apr. 2, 1985

[54] PROCESS FOR PREPARING OPTICALLY ACTIVE PENEMS

[75] Inventors: Marco Alpegiani; Carlo Battistini; Angelo Bedeschi; Giovanni Franceschi; Maurizio Foglio; Franco Zarini, all of Milan, Italy

[73] Assignee: Farmitalia Carlo Erba, Milano, Italy

[21] Appl. No.: 447,187

[22] Filed: Dec. 6, 1982

[30] Foreign Application Priority Data

Dec. 11, 1981 [GB] United Kingdom ............... 8137513

[51] Int. Cl.³ .................. C07D 499/00; A61K 31/425
[52] U.S. Cl. ........................ 260/245.2 R; 260/245.2 T
[58] Field of Search .................. 260/245.2 R; 424/270

[56] References Cited

U.S. PATENT DOCUMENTS

| | | | |
|---|---|---|---|
| 4,269,771 | 5/1981 | Lombardi et al. | 260/245.2 R |
| 4,331,677 | 5/1982 | Foglio et al. | 260/245.2 R |
| 4,348,320 | 9/1982 | Bouffard et al. | 260/265.2 R |

*Primary Examiner*—Nicholas S. Rizzo
*Attorney, Agent, or Firm*—Oblon, Fisher, Spivak, McClelland & Maier

[57] ABSTRACT

Processes for the preparation of a penem derivative of formula I

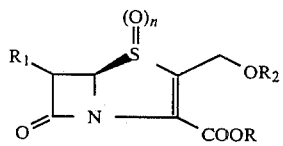

wherein n=0 or 1;
  R is a carboxy protecting group or H;
  $R_1$ is hydrogen, a hydrocarbon group substituted or unsubstituted, or lower alkoxy; and
  $R_2$ is hydrogen, $C_1$-$C_5$ alkyl, carbamoyl N-substituted by lower alkyl or unsubstituted, or an acyl group; and the pharmaceutically acceptable salts thereof.

These processes allow one to prepare stereospecifically only 5R derivatives, and are characterized by $R_2$-introduction at a very late stage in the synthesis, thereby enabling a great number of compounds of formula I to be prepared.

Penem derivatives are useful antibacterial agents.

2 Claims, No Drawings

PROCESS FOR PREPARING OPTICALLY ACTIVE PENEMS

This invention relates to processes for the preparation of compounds 1 of the formula I and their pharmaceutically acceptable salts:

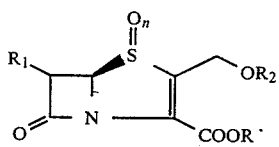

in which $n=0$ or 1,

R represents a hydrogen atom, a lower alkyl,2,2,2-trichloroethyl, acetonyl, allyl, benzyl, p-nitrobenzyl, p-methoxybenzyl, phenyl, o-nitrophenyl, benzhydryl or 1-phenoxyethyl group or a residue known to be hydrolysed "in vivo" and having favorable pharmacokinetic properties such as an acetoxy-methyl, pivaloyloxymethyl or phthalidyl group, or a group of the formula

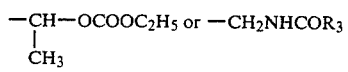

in which $R_3$ represents an alkyl group having from 1 to 5 carbon atoms or an aryl group such as phenyl or p-nitrophenyl;

$R_1$ represents a hydrogen atom, a lower alkyl, lower alkoxy, cycloalkyl, or hydroxyalkyl group, preferably a hydroxy substituted lower alkyl group such as 1-hydroxyethyl, the alcoholic function of the hydroxyalkyl group being free or protected, the protecting group (if present) preferably being a p-nitrobenzyloxycarbonyl, dimethyl-t-butylsilyl, diphenyl-t-butylsilyl, 2,2,2-trichloroethoxycarbonyl, trimethylsilyl, benzyl, p-bromophenacyl, triphenyl-methyl or pyranyl group; and $R_2$ represents a hydrogen atom, an alkyl group having from 1 to 5 carbon atoms, a carbamoyl or N— $C_1$ to $C_4$ alkyl substituted carbamoyl group, an alkanoyl group having from 2 to 6 carbon atoms, a $C_4$–$C_7$ cycloalkylcarbonyl group, or an arylcarbonyl group.

The 6-substituent may have either α or β orientation, α orientation being preferred. When $R_1$ is lower hydroxyalkyl, the carbon bearing the hydroxy function can be R or S, but preferably R.

The carbon atom in position 5 has only the R configuration.

When $R_1$ is a cycloalkyl group, it is preferably a $C_4$–$C_7$ monocycloalkyl group, and in particular cyclopentyl or cyclohexyl.

When $R_2$ is alkanoyl, it is preferably acetyl, either unsubstituted or in its turn substituted by a $C_2$–$C_6$ alkanoyl group, in particular acetyl.

When $R_2$ is a $C_1$–$C_5$ alkyl group, it is preferably methyl or ethyl.

When $R_2$ is an aryl carbonyl group, it is preferably substituted or unsubstituted phenyl carbonyl, the substituent being halogen, hydroxy, amino cyano, nitro, a lower alkyl, or a lower alkoxy group.

The compounds of formula I are prepared in accordance with the following reaction scheme, in which Ac represents an acetyl group, Ph represents a phenyl group, and PG represents a protecting group, preferably one selected from p-nitrobenzyloxycarbonyl, dimethyl-t-butyl-silyl, diphenyl-t-butyl-silyl, 2,2,2-trichloroethoxycarbonyl, trimethylsilyl, benzyl, p-bromophenacyl, triphenylmethyl, and pyranyl groups.

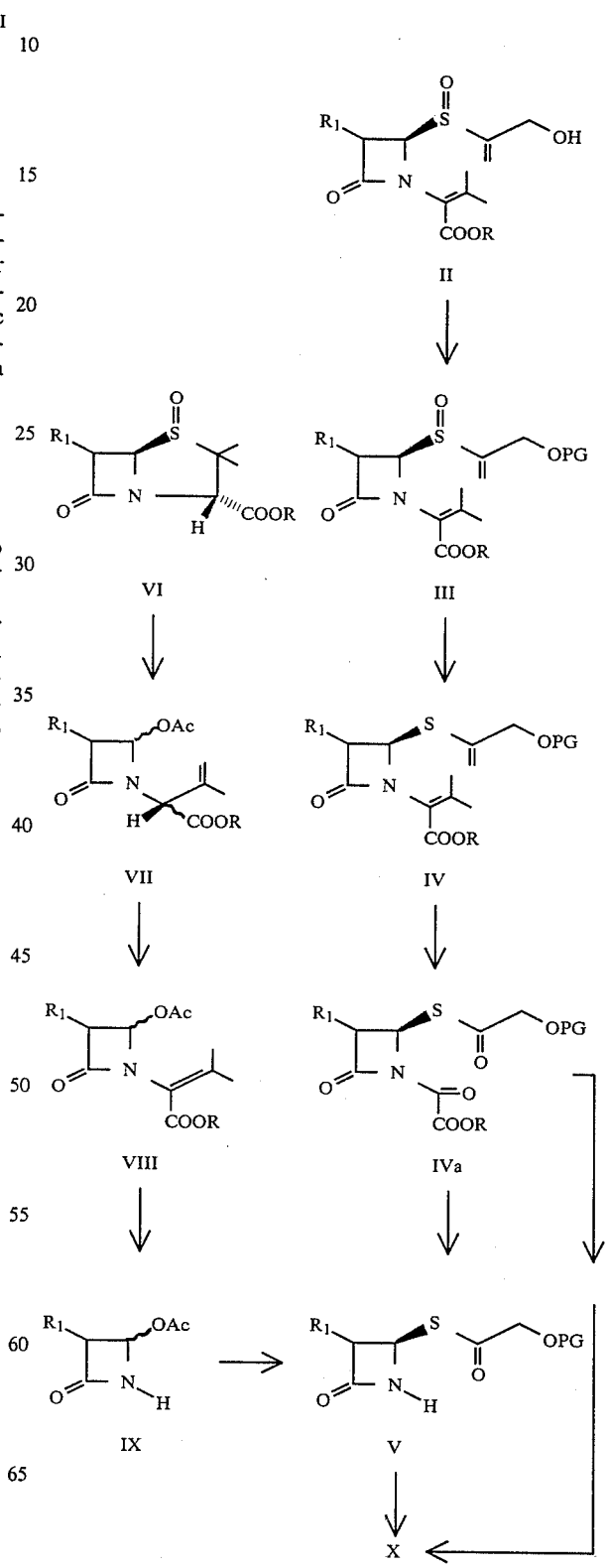

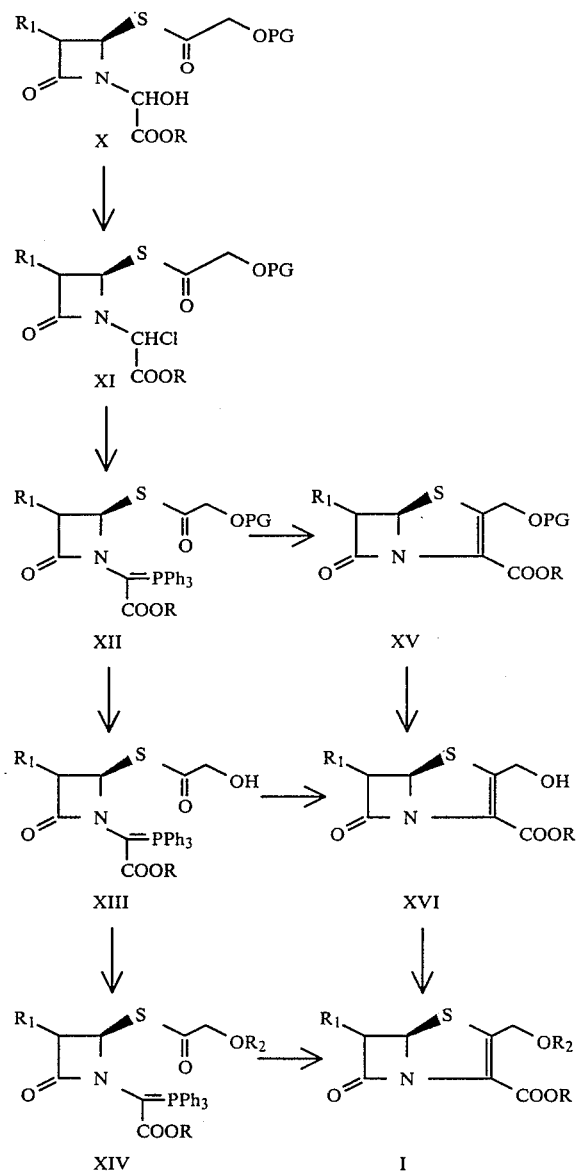

This invention offers three routes to compound X and three routes from compound XII to compound I. All routes pass through a common sequence of reactions for the conversion of compound X to compound XII.

The first route to compound X involves the protection of the free hydroxy group of compound II (prepared as described in British Pat. No. 2,043,639) with a protecting group, the reduction of the sulphoxide function in the resultant compound III, ozonolysis of both the carbon-carbon double bonds in the resultant compound IV, methanolysis of the N-substituent in the resultant compound IVa, and condensation of the resultant compound V with a glyoxylic ester of the general formula CHOCOOR wherein R is as defined above.

The reduction may be carried out using phosphorus tribromide at a temperature of from −40° to −20° C. in a suitable solvent such as anhydrous dimethylformamide.

The ozonolysis may be effected at a temperature of from −80° to −50° C. in a suitable solvent such as diethyl ether, methanol or, preferably, dichloromethane.

The methanolysis is preferably conducted in the presence of silica gel or of a catalytic amount of a strong base such as sodium methoxide.

The condensation of compound V with the glyoxylic ester is suitably carried out at elevated temperature, from 70° to 100° C. in an organic solvent such as benzene or toluene.

The second route to compound X follows the first route from compound II to compound IVa, but then bypasses compound V with a direct reduction of the oxamide function to a carbinolamide function. This can be achieved with zinc and acetic acid.

The third and most preferred route to compound X commences from compound VI, prepared as described in the aforesaid British patent. This compound VI may be converted to compound VII by treatment with acetic acid and trimethylphosphite in an inert solvent, such as toluene, under reflux. This reaction has been described by A. Suarato et al (Tet.Lett., 1978, 42, 4059–62). Isomerisation of the isopropenyl substituent of compound VII using a base, preferably triethylamine, in an inert organic solvent such as dichloromethane at from 0° to 20° C., leads to the compound VIII, and this latter may be converted to compound IX by ozonolysis and methanolysis steps analogous to those described above for the conversion of compound IV to compound V.

An alternative method of converting compound VIII to compound IX is the procedure described by E. G. Brain et al (J.C.S. Chem. Comm., 1972, 229). Compound IX is reacted with an O-protected hydroxythiolacetic acid of the general formula $HSCOCH_2OPG$, wherein PG is as above defined, to give compound V. This reaction is preferably conducted in an acetone:water mixture under basic conditions at from 0° to 20° C. Conversion then of compound V to compound X is as described for the first route.

The common sequence of reactions for the conversion of compound IX to compound XII comprises chlorination of compound X and reaction of the resultant compound XI with triphenylphosphine. The chlorination may suitably be effected with thionyl chloride at from −20° to 0° C. in an inert solvent such as tetrahydrofuran. The reaction with triphenylphosphine may be conducted at from 30° to 60° C., preferably 40° C., in an organic solvent such as tetrahydrofuran in the presence of a base such as pyridine or lutidine. Alternatively, the reaction may be conducted in the presence of silica gel at ambient temperature for a few hours.

Each of the three routes from compound XI to compound I comprises three steps: cyclisation, removal of the protecting group PG, and introduction of the desired group $R_2$. Naturally the introduction of the group $R_2$ follows the removal of the protecting group, and the three routes differ only in whether the cyclisation is carried out as the first, second or third of the three steps. The cyclisation is effected by heating under a nitrogen atmosphere at from 80° to 150° C. in an inert solvent such as benzene, toluene, or xylene.

The conditions for the removal of the protecting group PG depend upon the nature of the protecting group PG.

The group $R_2$ as above defined may be introduced by reaction with an anhydride or acyl chloride of the general formula $(R_2CO)_2O$ or $R_2COCl$ in which $R_2$ represents an alkyl group having from 1 to 4 carbon atoms or a cycloalkyl or aryl group; or by reaction with an isocyanate such as trichloroacetylisocyanate or chlorosulphonylisocyanate (leading to the compounds I in which $R_2$ represents a carbamoyl or substituted carbamoyl group); or with a diazoalkane having from 1 to 5 carbon atoms.

If the desired compound I is one in which $R_2$ represents a hydrogen atom, then the cyclisation is carried out as the first or second step of the three routes from compound XII, and the step of introducing the group $R_2$ is omitted. This is because compound XVI is compound I when $R_2=H$ and $N=0$. If the desired compound I is one in which n is 1, then the sulphur atom of the compound I obtained by one of the methods described may be oxidized in a conventional manner.

Two features of the present invention deserve special comment. The carbon atom in position 5, the R configuration of which is "the sole essential stereochemical requirement for antibiotic activity" (H. R. Pfaendler, J. Gosteli and R. B. Woodward, J. Am. Chem. Soc., 101, 1979, 6306), retains its configuration from compound II right through to compound I. The carbon-sulphur bond is not disturbed in any step. In the case of preparation from compound VI, the reaction of compound IX with the O-protected hydroxythiolacetic acid proceeds stereospecifically giving only the 3S, 4R azetidinone V. Secondly, the group $R_2$ is introduced at a very late stage in the synthesis, thereby enabling a great number of compounds of formula I to be prepared.

Compounds of formula I possess a wide spectrum of antibacterial activity as well as β-lactamase inhibiting activity, and are described and claimed in the British Pat. No. 2,043,639 referred to above.

The invention is still further illustrated by the following examples in which the abbreviations PNB for p-nitrobenzyl, TBDPS for t-butyl-diphenylsilyl, and TBDMS for t-butyl-dimethylsilyl are used for the sake of brevity.

EXAMPLE 1

4-Acetoxy-3R-(1R-p-nitrobenzyloxycarbonyloxyethyl)-azetidin-2-one

IX: $R_1=CH_3CH(OCOOPNB)$

A solution of 9.1 g (0.02 mole) of methyl 6α-(1R-p-nitrobenzyloxycarbonyloxy-ethyl) penicillanate 1-oxide (VI: $R=CH_3$, $R_1=CH_3CH(OCOOPNB)$ in 100 ml of toluene was treated with 4 ml (0.07 mole) of acetic acid and 13.4 ml of trimethylphosphite (13.4 ml).

The resulting mixture was refluxed for 3 hours, cooled to room temperature, washed with saturated sodium bicarbonate solution (3×50 ml), water (50 ml), dried over anhydous sodium sulphate, and evaporated in vacuo.

The oily residue obtained was purified by column chromatography (cyclohexane:ethyl acetate) to yield 4-acetoxy-3R-(1R-p-nitrobenzyloxy-carbonyloxy-ethyl)-1-(1-methoxycarbonyl-2-methyl-2-propenyl)-azetidin-2-one (VII: $R=CH_3$, $R_1=CH_3CH(OCOOPNB)$) as a light yellow oil (7.9 g, 85% yield.

The isopropenyl moiety of this compound was isomerized by treatment with triethylamine in dichloromethane at 5° C. to yield 4-acetoxy-3R-(1R-p-nitrobenzyloxycarbonyloxy-ethyl)-1-(1-methoxycarbonyl-2-methyl-1-propenyl)-azetidin-2-one (VIII: $R=CH_3$, $R_1=CH_3CH(OCOOPNB)$—92% yield).

The title compound was prepared as a mixture of cis and trans acetate starting from this material by the following synthetic methods:

METHOD A

To a solution of 2.46 g (5.29 mmol) of the compound VIII, prepared as described immediately above, in 200 ml of acetone was added a solution of 4.51 g (21.08 mmol) of sodium metaperiodate in 140 ml of water. 80 ml of 0.1M pH7 phosphate buffer was added, maintaining the temperature from 10° to 15° C. 65 mg (0.41 mmol) of potassium permanganate was added. The resulting mixture was stirred at room temperature for five hours. The precipitate was filtered off. The filtrate was concentrated to about 200 ml. The aqueous phase was extracted with ethyl acetate. The organic layer was collected, washed with brine, dried over anhydrous sodium sulphate and concentrated in vacuo. The residue was chromatographed over silica gel eluting with cyclohexane:ethyl acetate mixtures to give the title compound as a foam (1.48 g; 79%).

METHOD B

To a stirred solution of 1-(1-methoxycarbonyl-2-methyl-1-propenyl)-3 (R)- [1-(R)-p-nitrobenzyloxycarbonyloxyethyl]-4(R,S) acetoxy acetidin-2-one (7.9 g: 17 mmol) in acetone (180 ml), water (25 ml) and pH 7.0, 1M phosphate buffer (5 ml), potassium permanganate (5.37 g; 34 mmol) was added portionwise while maintaining the temperature at 15°-20° C. The mixture was stirred under nitrogen atmosphere at room temperature for 40 minutes. Organic solvent was eliminated by evaporating in vacuo. The aqueous phase was covered with ethyl acetate. The resulting mixture was stirred and treated with cold aqueous sodium thiosulphate to eliminate the excess of potassium permanganate. The organic layer was washed with brine, dried over sodium sulphate, and concentrated under reduced pressure. The resulting residue was purified by column chromatography to give the title compound (4.96 g; 83%).

METHOD C

4-Acetoxy-3(R)-[1(R)-p-nitrobenzyloxycarbonyloxyethyl]-1-(1-methoxycarbonyl-2-methyl-1-propenyl)-azetidin-2-one was transformed into the title compound by ozonolysis and subsequent methanolysis (75% overall yield).

IR (neat); 1770–1740 cm$^{-1}$

PMR (CDCl$_3$): 1.5 and 1.53 (3H, d, J=7 Hz); 1.98 and 2.1 (2H, s); 5.3 (1H, m); 5.88 and 5.95 (1H, d, J=1,5 and 4.0 Hz); 6.8 (1H, bs); 7.57 (2H, d, J=8 Hz); 8.25 (2H, d, J=8 Hz)

EXAMPLE 2

4 (R)-t-butyldiphenylsilyloxyacetylthio-3(S)-[1(R)-p-nitrobenzyloxycarbonyloxyethyl]azetidin-2-one

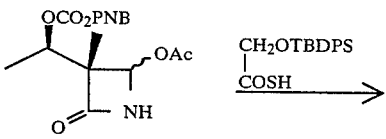

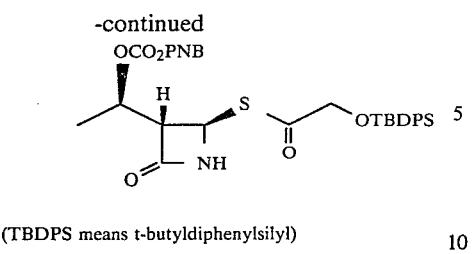

(TBDPS means t-butyldiphenylsilyl)

The thioacid (4.2 g) was dissolved in a solution of sodium hydroxide (0.56 g) in water (60 ml) at 5° C., after ten minutes, 4-acetoxy-3 (S)-[1(R)-p-nitrobenzyloxycarbonyloxyethyl]-azetidin-2-one (4.24 g) in CH₂Cl₂ was added.

The reaction mixture was vigorously stirred over 1 hour; diluted citric acid solution (70 ml) was added and the organic phase separated.

The aqueous phase was further extracted with ethyl acetate (3×50 ml). The combined organic extracts were dried (Na₂SO₄), evaporated, and chromatographed on silica gel, eluting with cycloexane/ethyl acetate, to obtain the title compound (4.42 g) as a white foam.

IR (neat): νmax 1770–1740, 1690 cm⁻¹

PMR (CDCl₃): 1.13 (9H, S); 1.48 (3H, d, J=7 Hz); 3.48 (1, dd, J=2, 6.5 Hz); 4.25 (2H, s); 5.2 (1H, m); 5.25 (2H,s); 5.31 (1H, d, J=2 Hz); 6.4 (1H, bs); 7.5–7.7 (12H, m); 8.22 (2H, d, J=8 Hz)

EXAMPLE 3

4(R)-t-butyl-diphenylsilyloxyacetylthio-3(S)-[1(R)-p-nitrobenzyl-oxycarbonyloxyethy]-1-(1-p-nitrobenzyloxy-carbonyl-1-hydroxymethyl)-azetidin-2-one.

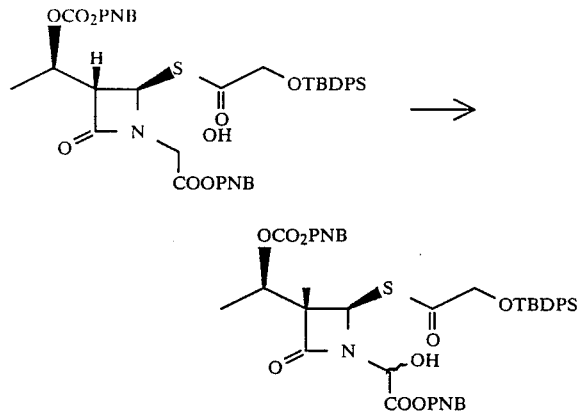

A solution of 4(R)l-t-butyldiphenylsilyloxyacetylthio-3(S)-[1(R)-p-nitrobenzyloxycarbonyloxyethyl]-azetidin-2-one (3.11 g, 5 mmole) and p-nitrobenzyl glyoxylate (3.20 g, 12.5 mmole) in benzene (100 ml) was refluxed, removing water by azeotropic distillation until almost to dryness (5 ml).

After refluxing for 2 hours, the reaction mixture was chromatographed on silica gel (ethyl acetate/cyclohexane) giving an epimeric mixture of carbinolamides.

EXAMPLE 4

4(R)-t-butyldiphenylsilyoxyacetylthio-3(S)-[1(R)-p-nitrobenzyloxycarbonyloxyethyl]-1-(1-p-nitrobenzyl oxycarbonyl-1-chloromethyl-azetidin-2-one

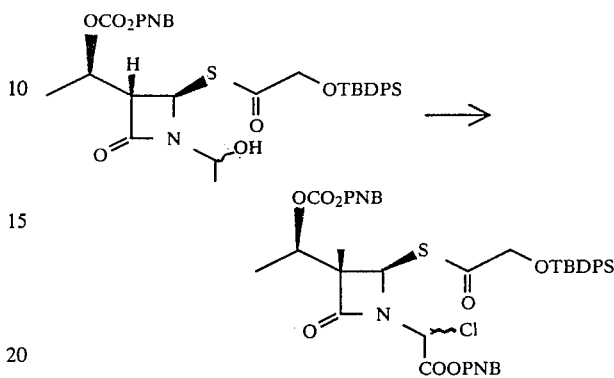

A stirred solution of 4(R)-t-butyl-diphenylsilyloxyacetylthio-3-(S)-[1-(R)-p-nitrobenzyloxycarbonyloxyethyl]-1-(1-p-nitrobenzyloxycarbonyl-1-hydroxymethyl)-azetidin-2-one (3.5 g, 4.2 mmole) in dry THF at 0° to −5° C. was treated with pyridine (0.48 ml, 6 mmole) and thionyl chloride (0.43 ml, 6 mmole).

After half an hour the reaction mixture was filtered and the filtrate was evaporated in vacuo to give the chloroesters as a yellow gum.

EXAMPLE 5

4-(R)-t-butyldiphenylsilyloxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one

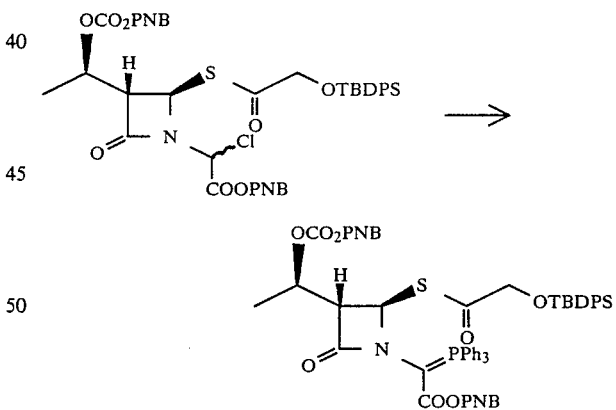

A solution in THF of 4(R)-t-butyldiphenylsilyoxyacetylthio-3(S)-[1(R)-p-nitrobenzyloxycarbonyloxyethyl]-1-(1-p-nitrobenzyloxycarbonyl-1-chloromethyl)-azetidin-2-one, obtained from the previous example, was treated with Ph₃P (2.2 g, 8.5 mmole) and silica gel (20 g).

The mixture was evaporated in vacuo to dryness and the resulting powder was left for two hours at room temperature. The powder was then charged on a top of a chromatographic column of silica gel and the phosphorane was eluted with cyclohexane/ethyl acetate mixtures to give the title product (3.2 g) as a light yellow foam.

EXAMPLE 6

4(R)-Hydroxyacetylthio-3(S)-[1(R)-p-nitrobenzyloxycarbonyloxyethyl]-1-(1-p-nitrobenzyloxycarbonyl-1-triphenylphosphoranylidene methyl)-azetidin-2-one

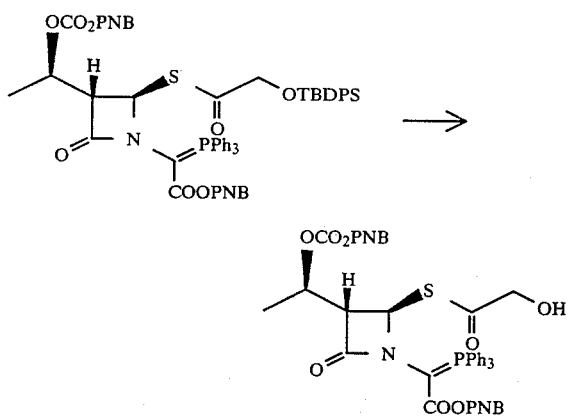

Trifluoracetic acid (4 ml) was added to a stirred solution of 4(R)-t-butyldiphenylsilyloxyacetylthio-3-(S)-[1(R)-p-nitrobenzyloxycarbonyloxyethyl]-1-(1-p-nitrobenzyloxycarbonyl-1-triphenylphosphoranylidenemethyl)-azetidin-2-one (1.07 g, 1 mmole) in ethyl acetate (50 ml). After fifteen minutes the solvent was removed, toluene (50 ml) was added and the solvent evaporated again to give the phosphonium salt (1.3 g) which was dissolved in THF (50 ml) and treated with 4 eq of tetrabutylammonium fluoride (TBAF).

After one hour the mixture was evaporated, dissolved in ethyl acetate (50 ml), and washed with saturated sodium hydrogen carbonate solution (3×25 ml) and water (25 ml).

The organic phase was separated, dried over anhydrous $Na_2SO_4$, and evaporated in vacuo. The oily residue was chromatographed on silica gel (cyclohexane/ethyl acetate) to give the title compound (0.75 g) as a foam.

EXAMPLE 7 p-Nitrobenzyl (5R)-2-hydroxymethyl-6(S)-[1(R)-p-nitrobenzyloxycarbonyloxyethyl]-2-penem-3-carboxylate

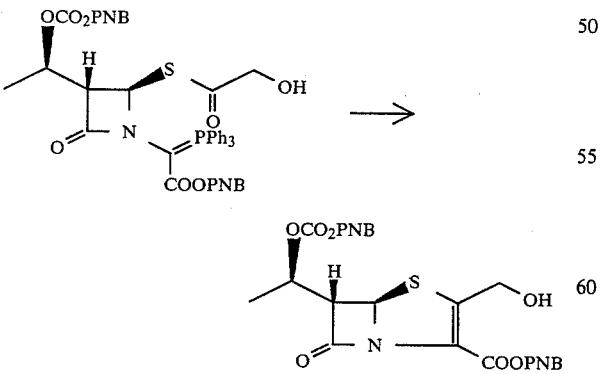

A solution of 4(R)-hydroxyacetylthio-3-(S)-[1(R)-p-nitrobenzyloxycarbonyloxyethyl]-1-(1-p-nitrobenzyloxycarbonyl-1-triphenylphosphoranylidenemethyl)-azetidin-2-one (0.6 g) in toluene (200 ml), together with a catalytic amount of hydroquinone, was refluxed for 2 hours.

The solvent was then evaporated in vacuo and the residue was purified by column chromatography on silica gel, eluting with toluene/ethyl acetate mixtures, to give the title product (0.42 g).

UV: λmax (EtOH 95%) 260 nm (ε19100); 319 nm (ε8400)

IR: νmax (CHCl$_3$) 3600–3200, 1790, 1745, 1710, 1605, 1580 cm$^{-1}$

PMR (CDCl$_3$): 1.51 (3H, d, J=7 Hz); 3.99 (1H, dd, J=2, 7.5 Hz); 4.69 (2H, bs); 5.15 (1H, m); 5.23 and 5.46 (2H, centers of ABq, J=14 Hz); 5.26 (2 H, s); 5.64 (1H, d, J=2 Hz); 7.51 (2H, d, J=8 Hz); 7.61 (2H, d, J=8 Hz); 8.20 (4H, d, J=8 Hz)

EXAMPLE 8 p-Nitrobenzyl (5R)-2-t-butyldiphenylsilyoxymethyl-6-(S)-[1-(R)-p-nitrobenzyloxycarbonyloxyethyl]-2penem-3-carboxylate

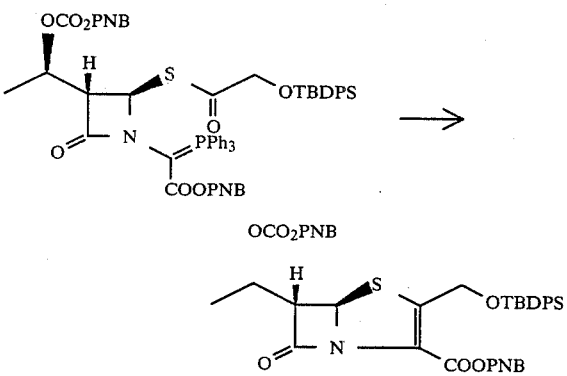

A solution of 4(R)-t-butyldiphenylsilyloxyacetylthio-3-(S)-[1(R -p-nitrobenzyloxycarbonyloxyethyl]-1-(1-p-nitrobenzyloxycarbonyl-1-triphenylphosphoranylidenemethyl)-azetidin-2-one (0.3 g) in dry toluene was refluxed for 3 hours.

The solvent was removed and the mixture was chromatographed on silica gel, eluting with cyclohexane/ethyl acetate mixtures, and thus affording the title compound (0.12 g).

EXAMPLE 9 p-Nitrobenzyl(5R)-2-hydroxymethyl-6(S)-[1(R)-p-nitrobenzyloxycarbonyloxyethyl]-2-penem-3-carboxylate

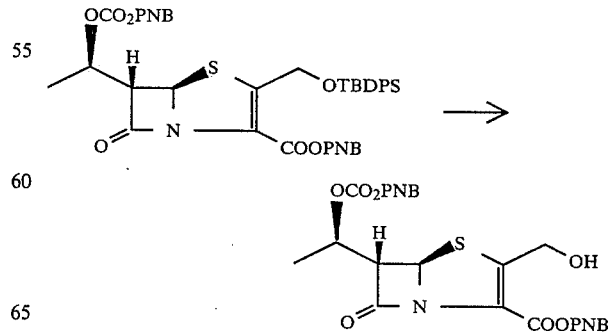

A solution of p-nitrobenzyl (5R)-2-t-butyldiphenylsilyloxymethyl-6(S)-[1(R)-p-nitrobenzyloxycarbonyloxyethyl]-2-penem-3-carboxylate (0.1 g) in THF was treated with 3 eq of TBAF at −15° C. under stirring.

The reaction mixture was then poured into ethyl acetate (50 ml) and washed with water (3×30 ml).

The dried organic phase was evaporated and chromatographed on silica gel, eluting with ethyl acetate/cyclohexane mixtures, to give the title compound (20 mg).

This material was proved to be identical with that obtained in Example 7.

EXAMPLE 10

Sodium (5R)-2-hydroxymethyl-6(S)-[1-(R)-hydroxyethyl]-2-penem-3-carboxylate

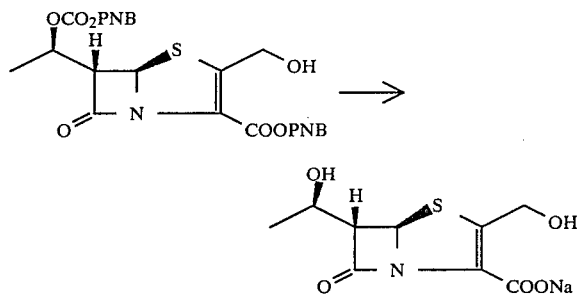

To a solution of 54 mg of p-nitrobenzyl (5R)-2-hydroxymethyl-6(S)-[(R)-p-nitrobenzyloxycarbonyloxyethyl]-2-penem-3-carboxylate in a mixture of ethyl acetate and water containing NaHCO₃ (6 mg), 5% Pd/C (40 mg) was added. The mixture was hydrogenated at atmospheric pressure for one hour. Another portion of 5% Pd/C (20 mg) was then added and left stirring for half an hour.

The mixture was filtered, the aqueous phase separated and washed with ethyl acetate. After evaporating the aqueous phase, the residue was purified on a reverse phase column eluting with water.

The title compound was obtained (12 mg) as an amorphous solid.

U.V.: $\lambda$max (EtOH 95%) 263 nm, 304 nm.

EXAMPLE 11 p-Nitrobenzyl (5R)-2-acetoxymethyl-6(S)[1(R)-p-nitrobenzyloxycarbonyloxyethyl]-2-penem-3-carboxylate

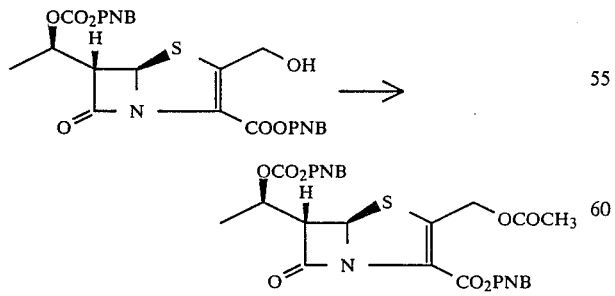

A solution of p-nitrobenzyl (5R)-2-hydroxymethyl-6(S)[1(R)-p-nitrobenzyloxycarbonyloxyethyl]-2-penem-3-carboxylate (350 mg, 0.58 mmole) in dry CH₂Cl₂ (5 ml) was sequentially treated with pyridine (140 mg) and acetic anhydride (80 mg) and then stirred at room temperature for six hours.

The mixture was washed with sodium hydrogen carbonate solution (3×5 ml) and water.

The dried organic phase was evaporated and the oily residue was chromatographed on silica gel, eluting with cyclohexane/ethyl acetate mixtures to give the title product (200 mg).

UV: $\lambda$max (ETOH 95%) 265, 321 nm
IR: (CHCl₃), $\nu$max 1795, 1750, 1715 1610, 1585 cm⁻¹
PMR (CDCl₃): 1.50 (3H, d, J=7 Hz); 2.11 (3H, s), 4.01 (1H, dd, J=1.8, 7.5 Hz); 5.11 and 5.50 (2H, centers of ABq, J=14 Hz); 5.15 (1H, m); 5.24 and 5.38 (2H, centers of ABq, J=12 Hz); 5.28 (2H,s); 5.28 (2H,s); 5.70 (1H, d, J=1.8 Hz) 7.55 (2H, d, J=8 Hz); 7.64 (2H, d, J=8 Hz); 8.22 (4H, d, J=8 Hz).

EXAMPLE 12

4(R)-acetoxyacetylthio-3(S)-[1(R)-p-nitrobenzyloxycarbonyloxyethyl]-1-[1-p-nitrobenzyloxycarbonyl-1-triphenylphosphoranylidenemethyl]-azetidin-2-one

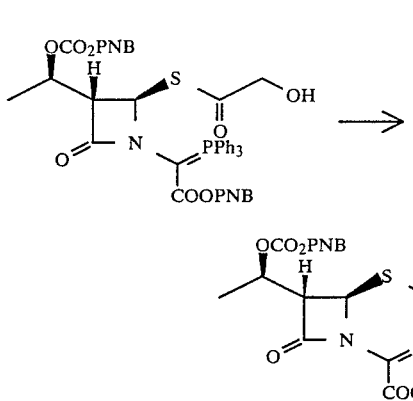

A stirred solution of 4(R)-hydroxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one (418 mg, 0.5 mmole) in CH₂Cl₂ (5 ml) was sequentially treated with pyridine (162 mg) and acetic anhydride (90 mg) and then stirred at room temperature for six hours.

The solution was washed with sodium hydrogen carbonate solution (3×5 ml) and water.

The dried organic phase was then evaporated in vacuo, leaving a gum which was purified by column chromatography to give the title phosphorane (300 mg).

EXAMPLE 13 p-nitrobenzyl (5R)-2-acetoxymethyl-6(S)-[1(R)-p-nitrobenzyloxycarbonyloxyethyl]-2-penem-3-carboxylate

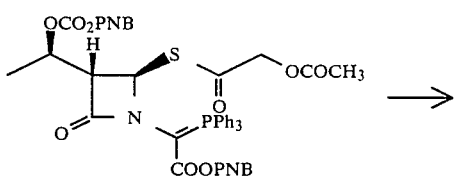

-continued

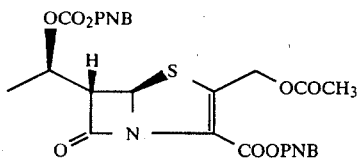

300 mg of 4 (R)-acetoxyacetylthio-3(S)-[1(R)-p-nitrobenzyloxycarbonyloxyethyl]-1-[1-p-nitrobenzyloxycarbonyl-1-triphenylphosphoranylidenemethyl]-azetidin-2-one were dissolved in toluene and the resulting solution was refluxed for 3 hours.

The solvent was removed and the mixture chromatographed on silica gel, eluting with ethyl acetate/cyclohexane, and thus affording the title penem (140 mg).

This product was proved to be identical with that obtained in Example 11.

EXAMPLE 14

Sodium (5R)-2-acetoxymethyl-6(S)-[1(R)-hydroxyethyl]-2-penem-3-carboxylate

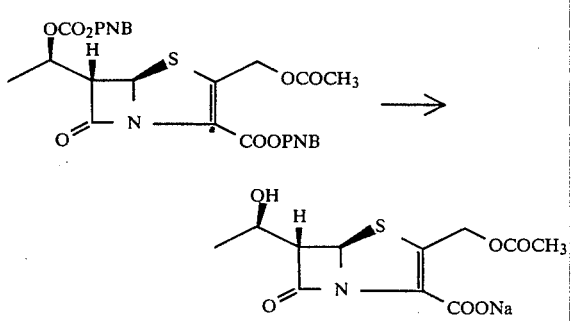

To a solution of 200 mg of sodium-(5R)-2-acetoxymethyl-6(S)-[1(R)-hydroxyethyl]-2-penem-3-carboxylate in a mixture of ethyl acetate and water containing NaHCO$_3$ (26 mg), 5% Pd/C (200 mg) was added and the resulting mixture was hydrogenated at atmospheric pressure for 1 hour. After this time, another portion of 5% Pd/C (100 mg) was added until complete absorption of H$_2$.

The resulting mixture was filtered and the aqueous phase was separated and washed with ethyl acetate.

The organic phase was discarded and the aqueous phase was evaporated in vacuo. The residue was purified on a reverse phase column eluting with water.

Evaporation of the aqueous solution afforded the title product as an amorphous solid (60 mg).

UV: λmax (EtOH 95%) 263 (ε4630); 305 (ε5500)

NMR: δppm (D$_2$O): 1.31 (3H, d, J=6.5 Hz); 2.19 (3H, s); 3.92 (1H, dd, J=1.5, 7.0 Hz); 4.21 (1H, m); 5.10 and 5.44 (2H, centers of ABq, J, 14 Hz), 5.67 (1H, d, J=1.5 Hz) [α]$_D$=+116.9° (c 0.1, EtOH 95%)

Analysis: C$_{11}$H$_{12}$NO$_6$SNa.H$_2$O requires C 40.37; H 4.31; N 4.28 Found; C 40.41; H 4.26; N 4.29

EXAMPLE 15

4(R)-(1-t-butyldimethylsilyloxymethylvinylthio)-3(S)-[1(R)-p-nitrobenzyloxycarbonyloxyethyl]-1-(1-methoxycarbonyl-2-methyl-1-propenyl) azetidin-2-one-8-oxide

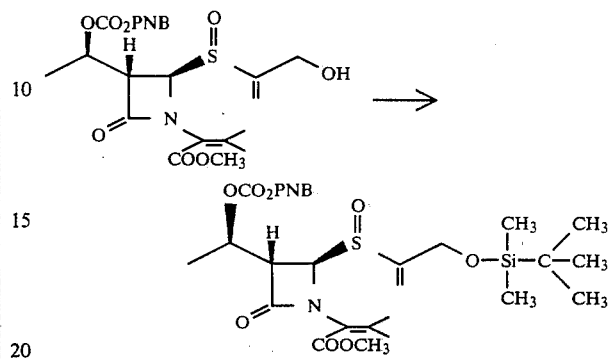

1.9 g of 4(R)-(1-hydroxymethylvinylthio)-3(S)-[1(R)-p-nitrobenzyloxycarbonyloxyethyl]-1-(1-methoxycarbonyl-2-methyl-1-propenyl)-azetidin-2-one-8-oxide were dissolved in 20 ml of dichloromethane. 0.7 ml of triethylamine, 640 mg of t-butyldimethylsilylchloride, and 20 mg of dimethylaminopyridine were added under nitrogen atmosphere.

After stirring overnight at room temperature, the solution was washed with water, ammonium chloride solution, and the solvent evaporated.

The residue was chromatographed on silica gel with cyclohexane-ethyl acetate (1:1), affording 0.83 g of the title compound PMR (CDCl$_3$)δ(ppm): 0.07 (s, 6H, Si(CH$_3$)$_2$) 0.88 (s, 9H, SiC(CH$_3$)$_3$) 1.41 (d, J=6.5 Hz, 3H, CH$_3$CH) 2.14 (s, 3H, CH$_3$) 2.30 (s, 3H, =CH$_3$) 3.75 (s, 3H, COOCH$_3$) 3.7-3.9 (m, 1H, H-6) 4.48 (bs, 2H, CH$_2$OSi) 5.25 (s, 2H, CH$_2$Ph) 5.1-5.2 (m, 2H, H-5, CH$_3$CH) 5.85 (bs, 1H, =H) 5.98 (bs, 1H, =H) 7.4-8.4 (m, 4H, PhNO$_2$)

I.R. (CH$_2$Cl$_2$), ν(cm$^{-1}$): 1730 C=O unsat. ester 1755 C=O OCOO 1780 C=O β-lactam mass spectrum (FD): m/e 624

EXAMPLE 16

4(R)-(1-t-butyldimethylsilyloxymethylvinylthio)-3(S)-[1(R)-p-nitrobenzyloxycarbonyloxyethyl]-1-(1-methoxycarbonyl-2-methyl-1-propenyl)azetidin-2-one

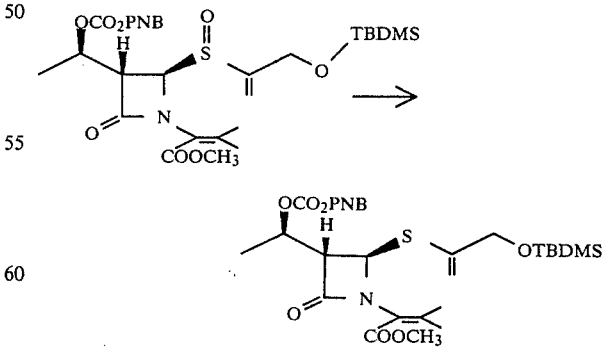

(TBDMS means t-butyldimethylsilyl)

A solution of 0.8 g of 4(R)-(1-t-butyldimethylsilyloxymethylvinylthio)-3(S)[1(R)-p-nitrobenzyloxycarbonyloxyethyl]-1-(1-methoxycarbonyl-2-methyl-1- propenyl)-azetidin-2-one-S-oxide in 30 ml of anhydrous dimethylformamide was cooled at −20° C. and 0.25 ml of phosphorous tribromide were added.

After 15 minutes, the mixture was diluted with ethyl acetate, washed twice with a saturated solution of NaHCO$_3$, then with water and dried (Na$_2$SO$_4$).

Evaporation of the solvent afforded 0.7 g of the title compound.

PMR (CDCl$_3$), δ (ppm): 0.05 (s, 6H, Si(CH$_3$)$_2$) 0.90 (s, 9H, SiC(CH$_3$)$_3$) 1.48 (d, J=6.5 Hz, 3H, CH$_3$CH) 2.01 (s, 3H, CH$_3$) 2.24 (s, 3H, CH$_3$) 3.35 (dd, J=2.5, 7.0 Hz, 1H, H-6) 3.73 (s, 3H, COOCH$_3$) 4.08 (t, J=2.0 Hz, 2H, CH$_2$OSi) 5.26 (s, 2H, CH$_2$Ph) 5.2–5.35(m, 3H, CH$_3$, CH, H-5, H) 5.56 (d, J=2.0, 1H, H) 7.4–8.4 (m, 4H, PhNO$_2$)

EXAMPLE 17

4(R)-t-butyldimethylsilyloxyacetylthio-3(S)-[1(R)-p-nitrobenzyloxycarbonyloxyethyl]-1-methoxy-oxaloyl-azetidin-2-one

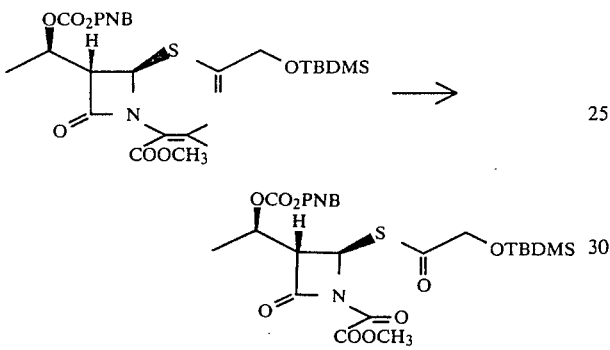

0.7 g of 4(R)-(1-t-butyldimethylsilyloxymethylvinyl-thio)-3(S)-[1(R)-p-nitrobenzyloxycarbonyloxyethyl]-1-(1-methoxycarbonyl-2-methyl-1-propenyl)-azetidin-2-one were dissolved in 30 ml of dichloromethane and 10 ml of methanol.

The solution was cooled to −78° C. and ozone in oxygen was bubbled through the solution until a blue color appeared.

After shaking with an aqueous solution of Na$_2$S$_2$O$_5$ and drying over Na$_2$SO$_4$, evaporation of the solvent gave 0.6 g of the title compound.

EXAMPLE 18

4(R)t-butyldimethylsilyloxyacetylthio-3(S)-[1(R)-p-nitrobenzyloxycarbonyloxyethyl]-azetidin-2-one

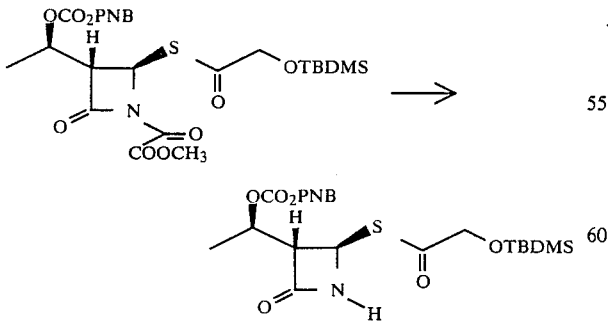

0.6 g of 4(R)-t-butyldimethylsilyloxyacetylthio-3(S)[1(R)-n-nitrobenzyloxycarbonyloxyethyl]-1-methoxyaloylazetidin-2-one were dissolved in 30 ml of methanol and a few grams of silica gel were added.

After stirring for 1 hour, the mixture was filtered and the solvent evaporated from the filtrate.

The residue was chromatographed on silica gel with cyclohexane-ethyl acetate (3:2) giving 0.28 g of the title compound.

PMR (CDCl$_3$), δ(ppm) 0.15 (s, 6H, Si(CHHD 3)$_2$) 0.95 (s, 9H, SiC(CH$_3$)$_3$) 1.45 (d, J=6.5 Hz, 3H, CH$_3$CH) 3.42 (dd, J=3.0, 6.0 Hz, 1H, H-6) 4.25 (s, 2H, CH$_2$OSi) 5.26 (s, 2H, CH$_2$Ph) 5.1–5.3 (m, 2H, CHCH$_3$, H-5) 6.70 (bs, 1H, NH) 7.4–8.4 (m, 4H, Ph,NO$_2$)

I.R. (CH$_2$Cl$_2$), ν(cm$^{-1}$): 1695 C=O 1750 —OCOO— 1785 β-lactam

EXAMPLE 19

4(R)-t-butyldimethylsilyloxyacetylthio-3(S)-[1(R)-p-nitrobenzyloxycarbonyloxyethyl]-1-(1-p-nitrobenzyloxycarbonyl-1-hydroxymethyl)-azetidin-2-one

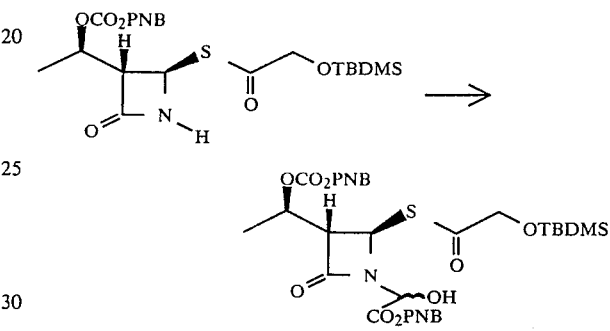

0.34 g of 4(R)-t-butyldimethylsilyloxyacetylthio-3(S)-[1(R)-p-nitrobenzyloxycarbonyloxyethyl]-azetidin-2-one and 0.34 g of p-nitrobenzyl glyoxylate in 10 ml of benzene were kept at refluxing temperature for two hours.

After evaporation of the solvent, purification of the residue by silica gel column chromatography, eluting with cyclohexane-ethyl acetate (3:2), afforded 0.27 g of the title compound.

PMR (CDCl$_3$), δ(ppm): 0.13 (s, 6H, Si(CH$_3$)$_2$) 0.95 (s, 9H, SiC(CH$_3$)$_3$) 1.47 (d, J=6.5 Hz, 3H, CH$_3$CH) 3.52 (m, 1H, H-6) 4.27 (s, 2H, CH$_2$OSi) 4.0–4.6 (m, 2H, CHOH, CH/OH) 5.25 (s, 4H, two CH$_2$Ph) 5.1–5.6 (m, 2H, CHCH$_3$, H-5) 7.3–8.3 (m, 8H, two Ph-NO$_2$)

EXAMPLE 20

4(R)-t-butyldimethylsilyloxyacetylthio-3(S)-[1(R)-p-nitrobenzyloxycarbonyloxyethyl]-1-(1-p-nitrobenzyloxycarbonyl-1-chloromethyl)-azetidin-2-one

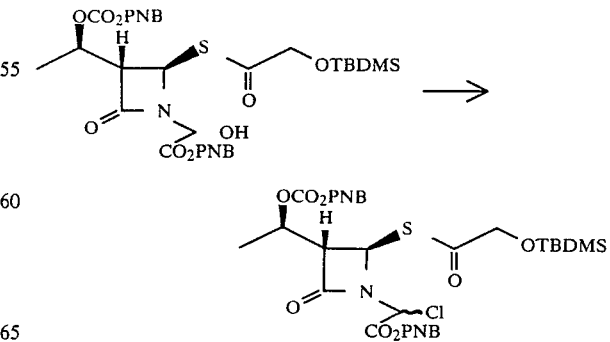

A solution of 0.27 g of 4(R)-t-butyldimethylsilyloxyacetylthio-3(S)-[1(R)-p-nitrobenzyloxycarbonyloxyethyl]-1-(1-p-nitrobenzyloxycarbonyl-1-hydroxymethyl)-azetidin-2-one in 3 ml of anhydrous tetrahydrofuran was cooled at 0° C. 0.045 ml of pyridine and 0.03 ml of thionyl chloride were added. After 10 minutes the mixture was filtered.

Evaporation of the solvent gave 0.3 g of the title compound which was used as such for the next step.

EXAMPLE 21

4(R)-t-butyldimethylsilyloxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one

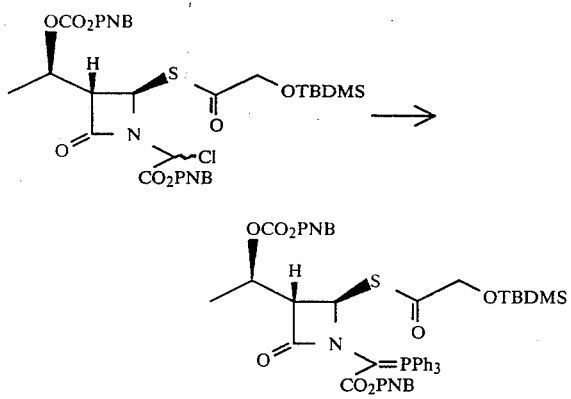

0.3 g of 4(R)-t-butyldimethylsilyloxyacetylthio-3(S)-[1(R)-p-nitrobenzyloxycarbonyloxyethyl]-1-(1-p-nitrobenzyloxycarbonyl-1-chloromethyl)-azetidin-2-one and 0.45 g of triphenylphosphine were dissolved in 5 ml of dichloromethane and 2-3 g of silica gel were added.

After evaporation of the solvent, the loaded silica gel was dried, left at room temperature overnight, and then washed with cyclohexane to remove the triphenylphosphine excess.

The product adsorbed on the silica was chromatographed on silica gel, eluting with cyclohexane-ethyl acetate 3:2.

0.26 g of the title compound were obtained.

PMR (CDCl$_3$), δ (ppm) 0.08, 0.15 (two s, 6H, Si(CH$_3$)$_2$) 0.89, 0.93 (two s, 9H, SiC(CH$_3$)$_3$) 1.35 (d, J=6.5 Hz, 3H, CH$_3$CH) 4.1-4.2 (m, 2H, CH$_2$OSi) 4.6-5.0 (m, 1H, CHCH$_3$) 5.20 (bs, 4H, two CH$_2$—Ph—NO$_2$) 7.56 (bs, 15H, P(Ph)$_3$) 7.6-8.4 (m, 8H, two Ph—NO$_2$)

EXAMPLE 22

4(R)-hydroxyacetylthio-3(S)-[1(R)-p-nitrobenzyloxycarbonyloxyethyl]-1-(1-p-nitrobenzyloxycarbonyl-1-triphenylphosphoranylidenemethyl)azetidin-2-one

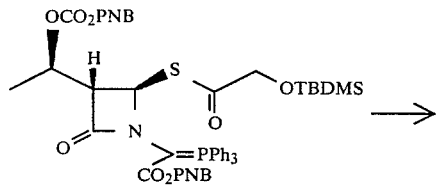

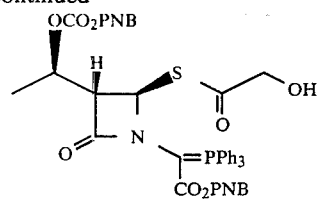

A solution of 0.26 g of 4(R)-t-butyldimethylsilyloxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one and 0.07 ml of acetic acid in 2 ml of anhydrous tetrahydrofuran was treated with a solution of 0.18 g of tetrabutylammonium fluoride in 2 ml of tetrahydrofuran.

After stirring at room temperature for 1 hour, the mixture was diluted with ethyl acetate, washed with water, saturated NaHCO$_3$ solution, and water again.

After drying and evaporation of the solvent, the residue was purified by silica gel column chromatography, eluting with cyclohexane-ethyl acetate (1:3), thus giving 0.13 g of the title compound.

PMR (CDCl$_3$), δ (ppm): 1.37 (d, J=6.5 Hz, 3H, CH$_3$CH) 4.2 (m, 2H, CH$_2$OH) 4.9 (m, 1H, CH$_3$CH) 5.25 (m, 5H, two CH$_2$Ph, H-5) 7.55 (s, 15H, P(Ph)$_3$) 7.6-8.4 (m, 8H, two PhNO$_2$)

EXAMPLE 23 p-nitrobenzyl (5R)-2-hydroxymethyl-6(S)-[1(R)-p-nitrobenzyloxycarbonyloxyethyl]-2-penem-3-carboxylate

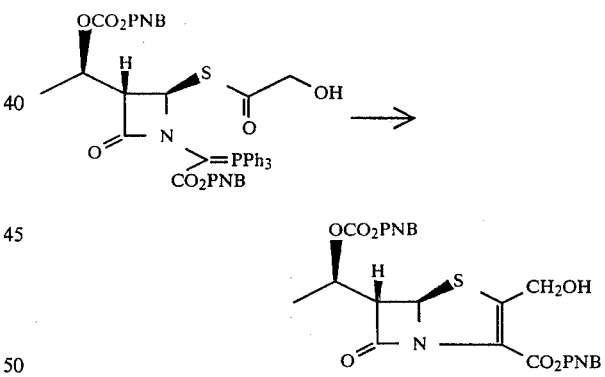

A solution of 0.13 g of 4(R)-hydroxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one in 10 ml of xylene was refluxed under nitrogen atmosphere for 1 hour.

Evaporation of the solvent and purification by preparative TLC (silica gel) afforded 50 mg of the title compound.

$[α]_D^{20}$ = +66° (c 1.3, CHCl$_3$)

PMR (CDCl$_3$), δ (ppm): 1.51(d, J=6.5, 3H, CH$_3$CH) 3.55 (bs, 1H, OH) 3.97 (dd, J=2.0, 8.0 Hz, 1H, H-6) 4.68 (s, 2H, CH$_2$OH) 5.19 (dq, J=6.5, 8.0 Hz, 1H, CHCH$_3$) 5.25-5.45 (m, 4H, two CH$_2$Ph) 5.65 (d, J=2.0 Hz, 1H, H-5) 7.4-8.5 (m, 8H, two PhNO$_2$) Mass spectrum (F.D.)m/1 559 U.V.: λ max (CH$_2$Cl$_2$): 269 nm (ε17.000), 323 (6800) I.R. (CH$_2$Cl$_2$) ν (cm$^{-1}$), 1795, 1755, 1710.

EXAMPLE 24 p-nitrobenzyl
(5R)-2-t-butyldimethylsilyloxymethyl-6(S)-[1(R)-p-nitrobenzyloxycarbonyloxyethyl]-2-penem-3-carboxylate

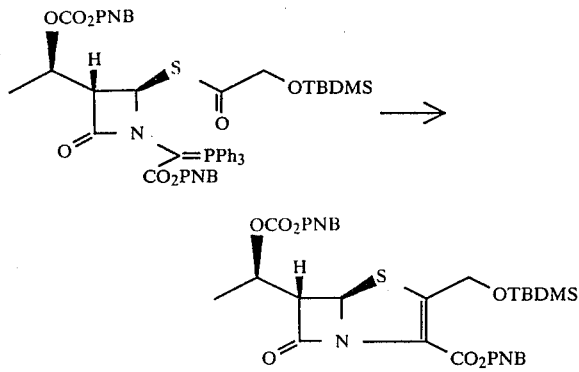

A solution of 0.15 g of 4(R)-t-butyldimethylsilyloxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one in 15 ml of xylene was stirred at reflux temperature under nitrogen atmosphere for 1 hour.

Solvent was evaporated and the residue purified by preparative TLC (silica gel) obtaining 70 mg of the title compound.

EXAMPLE 25 p-nitrobenzyl
(5R)-2-hydroxymethyl-6(S)-[1(R)-p-nitrobenzyloxycarbonyloxyethyl]-2-penem-3-carboxylate

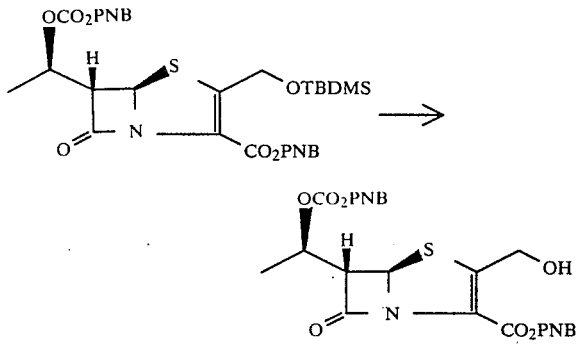

70 mg of p-nitrobenzyl(5R)-2-t-butyldimethylsilyloxymethyl-6(S)-[1(R)-p-nitrobenzyloxycarbonyloxyethyl]-2-penem-3-carboxylate were dissolved in 1 ml of anhydrous tetrahydrofuran, 0.025 ml of acetic acid and a solution of 68 mg of tetrabutylammonium fluoride in 0.5 ml of tetrahydrofuran were added.

The mixture was stirred at room temperature for 1 hour, diluted with ethyl acetate, washed with water, saturated NaHCO3 solution, and water again.

After evaporating the solvent, the residue was purified by silica gel preparative TLC, eluting with cyclohexane-ethyl acetate 3:7.

30 mg of the title compound were obtained, a material identical (IR and NMR spectra) with that obtained in Example 23.

EXAMPLE 26 p-nitrobenzyl(5R)-2-(N-trichloroacetylcarbamoyloxymethyl)-6(S)-[1(R)-p-nitrobenzyloxycarbonyloxyethyl]-2-penem-3-carboxylate

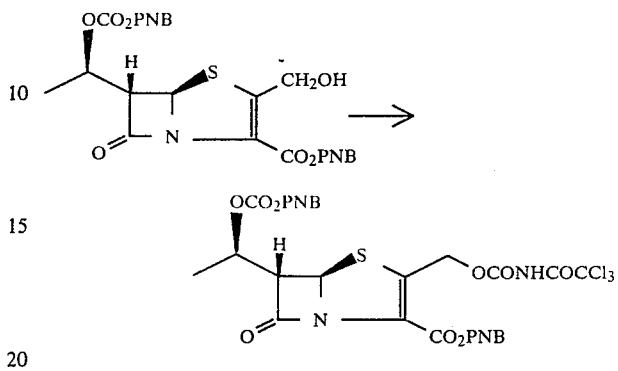

To a solution of 50 mg of p-nitrobenzyl (5R)-2-hydroxymethyl-6(S)-[1(R)-p-nitrobenzyloxycarbonyloxyethyl]-2-penem-3-carboxylate in 1 ml of purified acetone, cooled at 0° C., a solution of 0.06 ml of trichloroacetyl isocyanate in 1 ml of purified acetone was added dropwise.

After 20 minutes, evaporation of the solvent gave 100 mg of the crude title compound.

PMR (CDCl3) δ (ppm): 1.50 (d, J=6.0 Hz, 3H, CH3CH); 4.00 (dd, J=2.0, 8.0 Hz, 1H, H-6); 5.1–5.9 (m, 8H, H-5, CHO, two CH2Ph, CH2OCO); 7.5–8.4 (m, 8H, two PhNO2); 8.90 (bs, 1H, NH).

EXAMPLE 27 p-nitrobenzyl
(5R)-2-carbamoyloxymethyl-6-(S)-[1(R)-p-nitrobenzyloxycarbonyloxyethyl]-2-penem-3-carboxylate

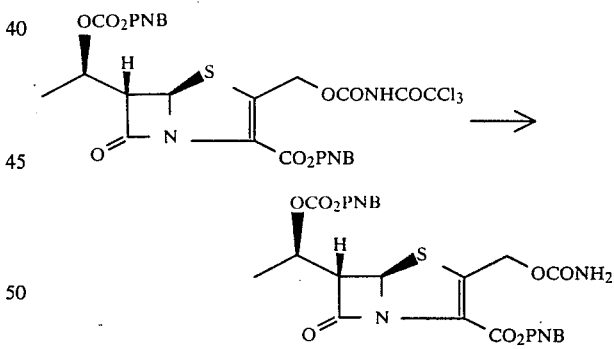

100 mg of crude p-nitrobenzyl (5R)-2-(N-trichloroacetylcarbamoyloxymethyl)-6(S)-[1(R)-p-nitrobenzyloxycarbonyloxyethyl]-2-penem-3-carboxylate were dissolved in 4 ml of methanol.

Silica gel (40–63 μm) was added and the mixture was stirred for 3 hours at room temperature and filtered, followed by washing with acetone.

After evaporation of the solvent from the filtrate, the residue was purified by silica gel preparative TLC, with cyclohexane-ethyl acetate 3:7 as eluent, giving 33 mg of the title compound.

$[\alpha]_D^{20} = +50°$ (c 2.4, acetone) PMR (CDCl3), δ(ppm): 1.48 (d, J=6.5 Hz, 3H, CH3CH) 3.95 (dd, J=2.0, 8.0 Hz, 1H, H-6) 4.85 (bs, 2H, NH2) 5.1–5.5 (m, 7H, CHCH3, two CH2Ph, CH2OCO) 5.64 (d, J=2.0 Hz, 1H, H-5) 7.4–8.5 (m, 8H, two PhNO₂) I.R. (KBr), ν(cm⁻¹): 1795, 1750, 1710.

EXAMPLE 28

4(R)-(N-trichloroacetylcarbamoyloxyacetylthio)-3(S)-[1-(R)-p-nitrobenzyloxycarbonyloxyethyl]-1-(1-p-nitrobenzyloxycarbonyl-1-triphenylphosphoranylidenemethyl)-azetidin-2-one

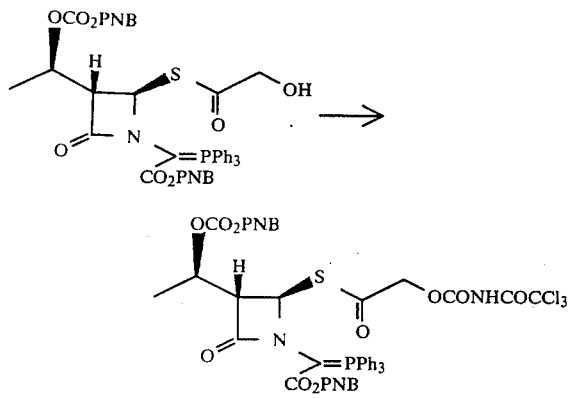

120 mg of 4(R)-hydroxyacetylthio-3(S)-[1(R)-p-nitrobenzyloxycarbonyloxyethyl]-1-(1-p-nitrobenzyloxycarbonyl-1-triphenylphosphoranylidenemethyl)-azetidin-2-one were dissolved in 2 ml of purified acetone and cooled at 0° C.

A solution of 0.1 ml of trichloroacetylisocyanate in 2 ml of purified acetone was added dropwise and the mixture was stirred for half an hour.

Evaporation of the solvent afforded 180 mg of the crude title compound.

EXAMPLE 29

4(R)-carbamoyloxyacetylthio-3(S)-[(R)-p-nitrobenzyloxycarbonyloxyethyl]-1-(1-p-nitrobenzyloxycarbonyl-1-triphenylphosphoranylidenemethyl)azetidin-2-one

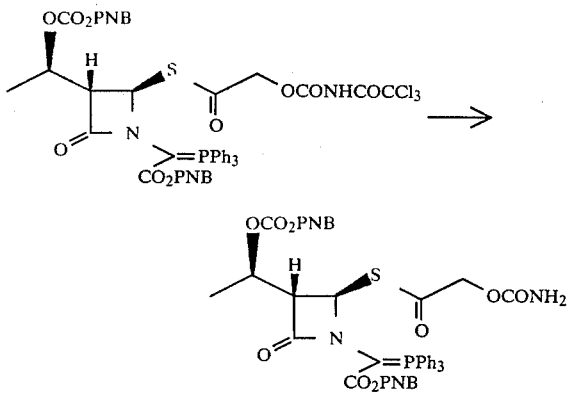

A mixture of 180 mg of crude 4(R)-(N-trichloroacetylcarbamoyloxyacetylthio)-3(S)-[1-(R)-p-nitrobenzyloxycarbonyloxyethyl]-1-(1-p-nitrobenzyloxycarbonyl-1-triphenylphosphoranylidenemethyl)-azetidin-2-one in 8 ml of methanol and silica gel (40–63 μm) was stirred for 4 hours at room temperature.

The mixture was filtered, washed with acetone, and the filtrate evaporated.

Purification of the residue by silica gel preparative TLC, using cyclohexane-ethyl acetate (1:4) as eluent, gave 70 mg of the title compound.

EXAMPLE 30 p-nitrobenzyl (5R)-2-carbamoyloxymethyl-6(S)-[1(R)-p-nitrobenzyloxycarbonyloxyethyl]-2-penem-3-carboxylate

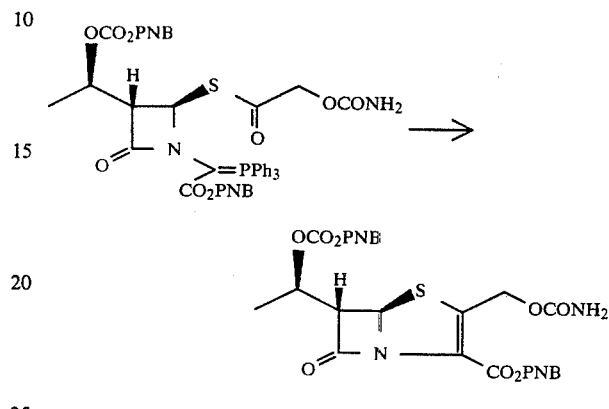

70 mg of 4(R)-carbamoyloxyacetylthio-3(S)-[1(R-p-nitrobenzyloxycarbonyloxyethyl]-1-(1-p-nitrobenzyloxycarbonyl-1-triphenylphosphoranylidenemethyl)-azetidin-2-one in 8 ml of xylene were heated at refluxing temperature for 1 hour under nitrogen atmosphere.

After evaporation of the solvent, purification of the residue by silica gel preparative TLC afforded 30 mg of the title compound, identical (IR and NMR spectra) with that obtained in Example 27.

EXAMPLE 31

Sodium (5R)-2-carbamoyloxymethyl-6(S)-[1(R)-hydroxyethyl]-2-penem-3-carboxylate

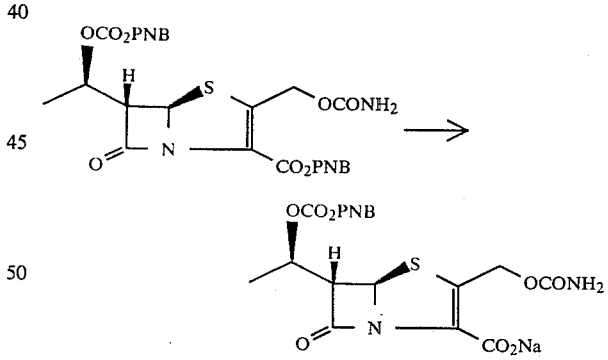

30 mg of p-nitrobenzyl (5R)-2-carbamoyloxymethyl-6(S)-[1(R)-p-nitrobenzyloxycarbonyloxyethyl]-2-penem-3-carboxylate were dissolved in 3 ml of ethyl acetate. 2 ml of water, 4.2 mg of NaHCO₃, and 45 mg of 5% palladium on charcoal were added and the mixture subjected to hydrogenation at room temperature for 2 hours.

After filtration through kieselguhr, the aqueous phase was washed with a small amount of cold ethyl acetate, filtered through Waters Sep-Pak C₁₈ cartridges, and lyophilized.

The residue was purified by reverse phase chromatography on Waters Sep-Pak C₁₈ cartridges, eluting with water.

8 mg of the title compound were obtained. UV: λmax (H$_2$O) 259 nm (ε 3600), 308 (5400) PMR (D$_2$O), δ (ppm): 1.31 (d, J=6.5 Hz, 3H, C$\underline{H}$$_3$CH); 3.91 (dd, J=1.5, 6.0 Hz, 1H, H-6): 4.25 (m, 1H, C$\underline{H}$OH); 5.02, 5.36 (two d, 2H, C$\underline{H}$$_2$OCO); 5.66 (d, J=1.5 Hz, 1H, H-5). [α]$_D^{20}$=+143° (c 0,97 H$_2$O).

What is claimed is:

1. A method for preparing a compound of formula

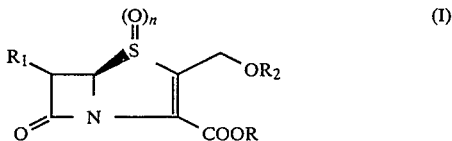

wherein n is 0 or 1; and wherein R is a hydrogen atom, a lower alkyl, 2,2,2-trichloroethyl, acetonyl, allyl, benzyl, p-nitrobenzyl, p-methoxybenzyl, phenyl, o-nitrophenyl, benzhydryl, 1-phenoxyethyl, acetoxymethyl, pivaloylmethyl or pthalidyl group or a group of the formula:

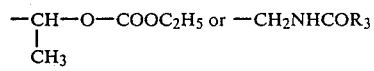

in which R$_3$ is an alkyl group having from 1 to 5 carbon atoms or an aryl group; R$_1$ is a hydrogen atom, a lower alkyl, lower alkoxy, cyclopentyl, cyclohexyl, or hydroxyalkyl group, wherein the hydroxyalkyl group has an unblocked alcohol group or an alcohol group which is blocked by a protective group selected from the group consisting of p-nitrobenzyloxycarbonyl, dimethyl-t-butylsilyl, diphenyl-t-butylsilyl, 2,2,2-trichloroethoxycarbonyl, trimethylsilyl, benzyl, p-bromophenacyl, triphenylmethyl or pyranyl groups; and R$_2$ is a hydrogen atom, an alkyl group having from 1 to 5 carbon atoms, a carbamoyl or N-C$_1$-C$_4$ alkyl substituted carbamoyl group, an alkanoyl group having from 2 to 6 carbon atoms, a C$_4$-C$_7$ cycloalkylcarbonyl group or an arylcarbonyl group selected from the group of unsubstituted phenylcarbonyl or phenyl carbonyl having the phenyl group substituted with a halogen, hydroxy, amino, cyano, nitro, lower alkyl or lower alkoxy group; and pharmaceutically acceptable salts thereof, said method consisting of:

(i) reacting a compound of the formula (V)

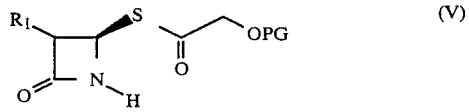

wherein R$_1$ is as defined above and PG is a protecting group as defined above; with a compound of the formula CHOCOOR, wherein R is as defined above at a temperature of from 70° to 100° C., (ii) chlorinating the resultant compound of step (i), having the formula (X):

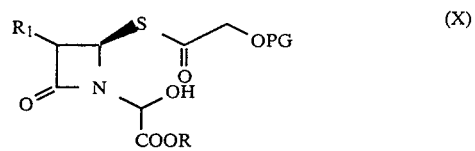

(iii) reacting the resultant compound of step (ii), having the formula (XI):

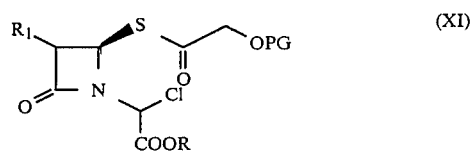

wherein R$_1$, R and PG are as defined above, with triphenylphosphine at a temperature of from 30° to 60° C., and (iv) converting the resultant compound of step (iii), having the formula (XII):

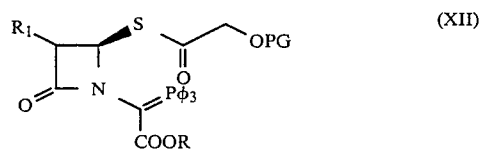

with a compound having the formula (I) as defined above, by the following steps (a) to (c):

(a) cyclizing by heating under nitrogen atmosphere at a temperature of from 80° to 150° C. in an inert solvent, (b) removing the protecting group PG from the substituent of the moiety:

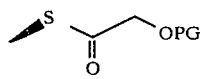

and, (c) introducing the group R$_2$, which is as defined above into the resultant moiety of step (b):

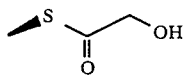

wherein step (a) is carried out after step (b) and before step (c), or step (a) is carried out after steps (b) and (c), or step (b) is omitted when R$_2$ is a hydrogen atom and step (a) is carried out before or after step (c); and further wherein said compound of the formula (V) in step (i) is prepared by protecting the hydroxy group of a compound having the formula (II)

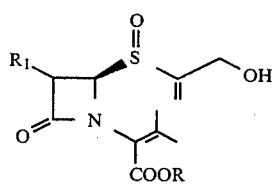

wherein $R_1$ and R are as defined above, with a protecting group, PG, which is as defined above; reducing the resultant compound having the formula (III)

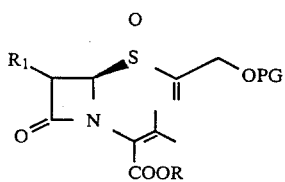

wherein R, $R_1$ and PG are as defined above, with phosphorous tribromide, ozonolyzing the resultant compound having the formula (IV)

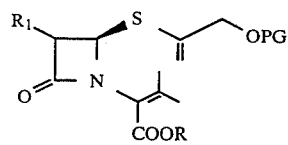

wherein R, $R_1$ and PG are as defined above, in a solvent at a temperature of from −80° to −50° C.; and methanolyzing the resultant compound having formula (IVa)

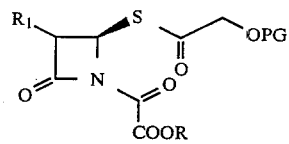

wherein R, $R_1$ and PG are as defined above, in the presence of silica gel to give a compound having formula V.

2. The method according to claim 1, wherein $R_3$ is an aryl group selected from the group of phenyl or p-nitrophenyl.

* * * * *